United States Patent [19]
Schweizer

[11] Patent Number: 6,086,569
[45] Date of Patent: Jul. 11, 2000

[54] HYPODERMIC SYRINGE

[76] Inventor: Kenneth M. Schweizer, 637 Tremont St., Sarasota, Fla. 34242

[21] Appl. No.: 09/304,701

[22] Filed: May 4, 1999

[51] Int. Cl.[7] .................................................. A61M 5/315
[52] U.S. Cl. ......................... 604/227; 604/181; 604/187; 604/218; 604/232
[58] Field of Search .................................. 604/181, 187, 604/218, 232, 208, 234, 227, 182

[56] References Cited

U.S. PATENT DOCUMENTS

| | | |
|---|---|---|
| 3,583,399 | 6/1971 | Ritsky . |
| 4,030,497 | 6/1977 | Binard et al. . |
| 4,064,879 | 12/1977 | Leibinsohn . |
| 4,340,051 | 7/1982 | Leibinsohn . |
| 4,439,185 | 3/1984 | Lundquist . |
| 4,465,474 | 8/1984 | Mardorf et al. . |
| 4,624,658 | 11/1986 | Mardorf et al. . |
| 4,624,659 | 11/1986 | Goldberg et al. . |
| 4,929,238 | 5/1990 | Baum ...................................... 604/208 |
| 4,952,205 | 8/1990 | Mauerer et al. . |
| 4,955,947 | 9/1990 | Hajianpour . |

*Primary Examiner*—Wynn Wood Coggins
*Assistant Examiner*—Michael M Thompson
*Attorney, Agent, or Firm*—Charles J. Prescott

[57] ABSTRACT

A hypodermic syringe for medical, dental or veterinary use of a conventional nature or employing prefilled cartridge ampules of injectable fluid. The syringe is arranged to allow the operator to automatically sense the amount of pressure being manually exerted by thumb pressure to express the fluid from the ampule or a fluid chamber into the patient. A slender elongated plunger mounted within the main body of the syringe is slidably moveable by thumb pressure against a thumb ring disposed at a distal end of the plunger. A spring-biased pressure indicator member is slidably moveable rearwardly for limited longitudinal movement with respect to the thumb ring and is deflected into the thumb of the operator a distance proportional to the fluid pressure at the syringe needle tip. The operator can thus sense indicia of fluid pressure produced while pressing the thumb ring to make an injection. Upon release of the plunger, the pressure indicator member is automatically retracted into its normal concealed position and away from the operator's thumb.

4 Claims, 3 Drawing Sheets

6,086,569

HYPODERMIC SYRINGE

BACKGROUND OF THE INVENTION

1. Scope of Invention

This invention relates generally to hypodermic syringes and particularly to an improvement in the hypodermic syringe handle for sensing manual thumb force proportional to medication injection flow rate and pressure.

2. Prior Art

An operator in making an injection determines the rate of speed of medication injection. It is known that the faster a fluid is injected into tissue, the more painful it can be for the recipient of the injection. Inadvertent hasty injections are commonplace. If there were a consistent way to determine the flow rate and pressure applied to the fluid in the ampule which is being injected out the needle tip, it would be possible to sense the amount of pressure that should be applied to the plunger, thus allowing the operator to push fluid from the ampule at a flow rate and pressure just shy of the threshold at which pain is sensed.

In the medical, dental and veterinary fields, cartridge ampules of injectable fluid are now commonly used in hypodermic syringes. Such ampules usually comprise a cylindrical container of glass or clear plastic material, the forward end of which is sealed by a rubber membrane and the rear end of which is sealed by a rubber piston which is slidable within the container. In use, such cartridge ampules are positioned within the barrel of a syringe so that the membrane is pierced by the rear end of a needle and the rubber piston is advanced into the container by manual thumb force against a thumb-operated plunger to inject the fluid through the needle into the patient.

It is commonly known among those who administer medicines or anesthetics subcutaneously or intramuscularly, that pain can be elicited due to a number of factors such as the number of pain receptors at the injection site, fluid temperature, the liquid agent being administered, and the speed or flow rate and pressure at which the agent is being administered.

Little can be done to control the site-specific area where the medicine is to be administered. The use of topical agents can help reduce the pain from the needle puncture wound, but this is not always successful. The medicine can sometimes be warmed to body temperature, thus reducing the pain elicited from the dissimilar temperature between the medicine and site. This too does not always work, since many medicines cause pain simply by being administered. It is a well-known fact that administering the medicine more slowly can often ease the amount of pain that is elicited at the site, in particular with injectable anesthetics.

The difficulty many operators have while administering injectable medicines is the lack of tactile sensitivity relating to how hard or how much pressure should be applied to push the syringe plunger to express the medicine, especially when there is an apprehensive patient or when the practitioner loses tactile feel because of the use of gloves for barrier protection.

One solution to this problem provided by the present invention is to create a device whereby the individual administering the injectable medicine consistently senses an indicator of the amount of applied injection pressure and, thusly, medication flow rate. After the needle has been inserted into the area to be injected in a conventional manner, the syringe plunger thumb ring or plate is depressed to create the necessary pressure to express the medicine from the ampule into the tissue or site. The invention allows the operator to apply a consistent reproducible pressure at a threshold just shy of that at which pain can be sensed. As a result, injections are more consistent and smooth, resulting in a comfortable injection for the patient. At the same time, this consistency builds operator confidence which yields decreased stress for the operator while performing the injection.

BRIEF SUMMARY OF THE INVENTION

This invention is directed to a hypodermic syringe for medical, dental or veterinary use preferably of the type employing prefilled cartridge ampules of injectable fluid. The syringe is arranged to allow the operator to automatically sense an indicator of the amount of pressure being manually exerted to express the fluid from the ampule or a fluid chamber of a conventional syringe into the patient. An elongated plunger is slidably moveable by thumb pressure against a thumb ring or plate disposed at a rearward end of the plunger to express the medication from the ampule or fluid chamber. A spring-biased pressure indicator member connected to or formed with the rearward end of the plunger, is slidably mounted for limited longitudinal movement with respect to the thumb ring and is deflected rearwardly through an aperture in the thumb ring against the thumb of the operator a distance proportional to the fluid pressure within the ampule or fluid chamber and, thusly, at the syringe needle tip. The operator can thus sense indicia of fluid pressure produced while pressing the thumb ring to make an injection. Upon release of the thumb ring, the pressure indicator member is automatically retracted into its normal concealed position and away from the operator's thumb.

The action of this invention is such that, when pressure is applied to the syringe thumb ring or plate by the operator to produce the injection of medication, the counter-acting spring contained within another housing or cover at the rearward end of the elongated plunger immediately adjacent the thumb ring or plate is compressed causing the slender pressure indicator member to protrude through a small hole in the thumb ring and to contact the operator's thumb. It is this contact that allows feedback to the operator. As more pressure is applied, more of the end of the pressure indicator member protrudes through the thumb ring. The feedback the operator feels against the thumb is in substantially direct proportion to the fluid pressure within the ampule or fluid chamber. In this way, the operator can sense and learn the appropriate amount of pressure that should be applied to the fluid within the ampule as it is being injected so as to cause no pain associated with fluid injection. When excess pressure is being applied, the user is so warned to more slowly administer the medication, producing less or no pain. The spring provided within a housing at the rear end of the plunger which maintains the pressure indictor member in a concealed at-rest position when no pressure is being applied to the thumb ring may be changed to suit the operators preference.

It is therefore an object of this invention to provide a syringe which includes a thumb-felt indicator of fluid pressure within the ampule or fluid chamber as medication is being injected.

It is another object of this invention to provide a pressure indicator member for a syringe which advises the operator in substantial direct proportion to the fluid pressure build-up within the ampule or fluid chamber as medication is injected.

It is still another object of this invention to provide a syringe which will help to educate the operator as to the thumb pressure level applied during medication injection beyond which the medication injection becomes painful.

In accordance with these and other objects which will become apparent hereinafter, the instant invention will now be described with reference to the accompanying drawings.

DETAILED DESCRIPTION OF THE INVENTION

Figure 1:
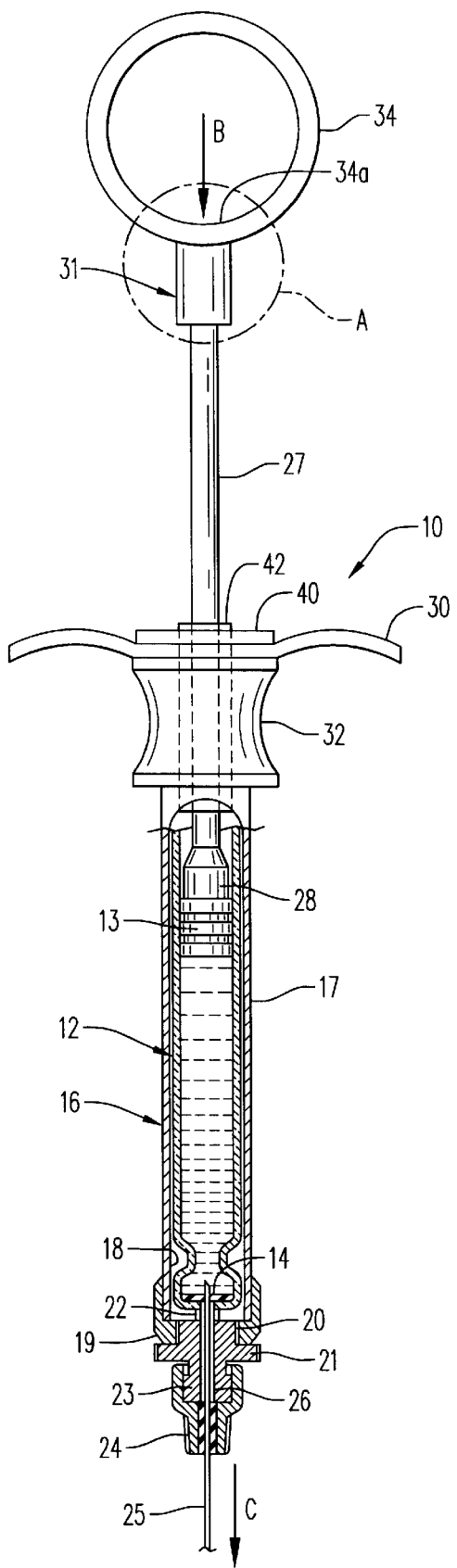
FIG. 1 is a longitudinal partial section view of an ampule-type hypodermic syringe according to the invention.

Referring now to the drawings, a typical cartridge ampule containing an injectible medication is shown generally at numeral 12 in conjunction with the preferred embodiment of the invention shown generally at numeral 10. The ampule 12 is of known kind which comprises a container defined generally by a cylindrical glass wall sealed at one end thereof by a rubber piston 13 and at the other end thereof by a rubber membrane 14. The injectible fluid is sealed in the container between the piston 13 and the membrane 14.

The syringe 10 generally includes a cylindrical barrel assembly 16 defining a cavity 18 to receive the cartridge ampule 12 and an elongated plunger 27. As is common practice, a cylindrical thin-wall body member 17 of barrel assembly 16 is formed with a large axially extending aperture (not shown) in its side wall to permit insertion and removal of the ampule 12. The forward end of the body member 17 is secured to a fitting 19 formed with a central axially directed screw fitted opening 20. An adapter 21 in threaded engagement with the opening 20 is formed with a central stud 22 projecting rearwardly into the cavity 18. A front end of the adapter 21 is formed with a spigot 23 which is in threaded engagement with a hub 24 which carries an axially extending hypodermic needle 25. The needle 25 extends rearwardly from the hub through an axial bore 26 in the adapter and the stud 22 and extends into cavity 18 beyond the stud 22.

The rear end of the body member 17 is received into a fitting 32 which carries a pair of laterally extending finger grips 30 held for free rotation by flanged fitting 40 which is connected to fitting 32. A bushing 42 in threaded engagement with the fitting 32 is formed with a central bore within which the plunger 27 is slidably and supportively received. The forward end of the plunger 27 carries an enlarged head 28 adapted to engage the rubber piston 13 of the ampule 12. The plunger 27 may be urged forwardly by means of a thumb ring 34 or plate carried on the rear end thereof. In the retracted position of the plunger 27, the head 28 is sufficiently withdrawn to facilitate ampule insertion and removal.

After ampule installation into the barrel assembly 16, forward pressure applied to the thumb ring 34 forces the ampule 12 forward into fluid communication with a rearward end of the hypodermic needle 25 which pierces through membrane 14. Further pressure will now cause the piston 13 to be advanced within the ampule 12 so that the fluid from the ampule becomes pressurized and is ejected from the needle 25. Upon release of the thumb ring 34, fluid pressure within the ampule 12 is reduced to zero.

Figure 2:
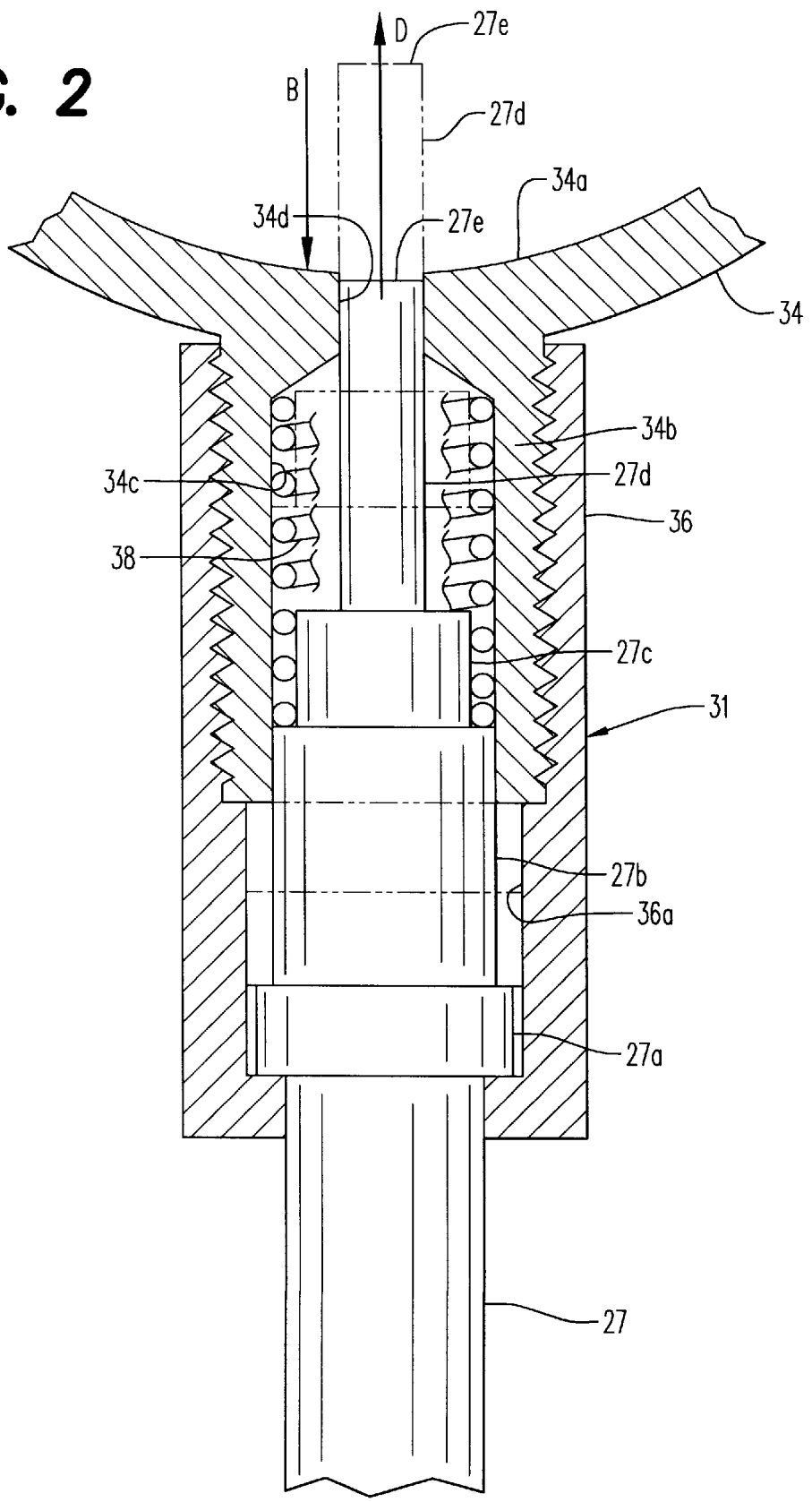
FIG. 2 is an enlarged section view of area A of FIG. 1.

Positioned at the rearward end of plunger 27 immediately adjacent the thumb ring 34 as best seen in FIG. 2 is a pressure indicator assembly shown generally at numeral 31. This pressure indicator assembly 31 includes a cylindrical outer housing 36 which is threadably engaged onto an inner housing 34b which is connected to or formed as a unit with thumb ring 34. Slidably positioned within a bore 36a of the outer housing 36 is an indicator shaft 27d of plunger 27. An enlarged shoulder 27a provides a forward stop in movement of the plunger 27 with respect to the outer housing 36. Cylindrical surface 27b is slidably engaged within bore 34c of the inner housing 34b. An elongated slender distal tip or shaft 27d, substantially smaller in diameter than plunger 27 itself, is positioned within a slidably mating aperture 34d and is held in an at-rest concealed position by a compression spring 38.

When in the at-rest position, the distal end surface 27e shown in solid lines in FIG. 2 is substantially continuous with the inner surface 34a of thumb ring 34. However, as thumb pressure is applied in the direction of arrow B to effect ejecting of liquid medication from the ampule 12, the pressure indicator member 27d begins to move in the direction of arrow D with respect to thumb ring 34 so that the pressure indicator member 27d begins to protrude as shown in phantom against the thumb of the operator. When a maximum thumb pressure is exerted in the direction of arrow B, the slender distal indicator member 27d will become fully extended against the spring biased pressure exerted by spring 38. The selection of spring stiffness of compression spring 38 should be selected such that, when this fully extended position is achieved, the thumb pressure exerted in the direction of arrow B is near to a maximum desirable fluid pressure within the ampule beyond which pain will be perceived by the patient receiving the injected fluid.

With only short practice, the operator will be able to quickly establish a relationship between the amount of protrusion of pressure indicator member 27d against thumb pressure to establish a relationship between that felt protrusion and fluid pressure within the ampule. Thereafter, the operator will be able to immediately sense a fluid pressure below which pain is not felt and beyond which the discomfort of excess pressure and fluid flow into the patient will result in discomfort.

Although the distal end 27e is shown flat, a pointed end may also be provided for enhanced thumb sensation of fluid pressure within the ampule. Such a pointed distal end should not be sufficiently sharp to cause pain to the operator, but should enhance the sensation of felt thumb pressure by such a pointed distal end which will obviously enhance sensitivity to fluid pressure within the ampule. However, transverse size or surface area of distal end 27e may vary widely so long as the amount of protrusion of the pressure indicator member 27d proportionately reflects medication injection pressure.

Figure 3:
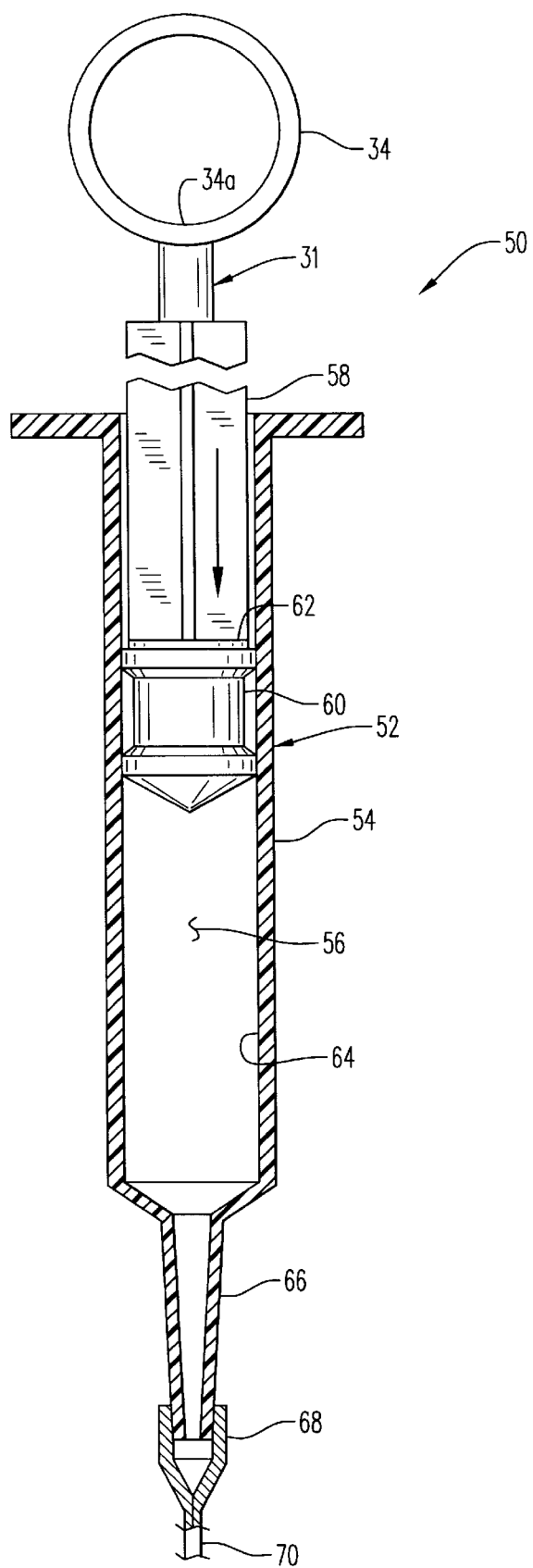
FIG. 3 is a longitudinal partial section view of a conventional hypodermic syringe according to the invention.

Referring now to FIG. 3, another embodiment of the invention is there shown generally at numeral 50 representing a syringe of a conventional type, either disposable or reusable in nature. The syringe 50 generally includes a barrel assembly 52 having a hollow body member 54 which defines a fluid chamber 56 for retaining fluid medication. The syringe assembly 50 also includes an elongated plunger 58 having a flexible piston or plug 60 attached adjacent one end 62 of the plunger 58 received into the open end of the chamber 56. The piston 60 sealably engages against an inner cylindrical surface 64 of the body member 54, the plunger 58 being pushable into the fluid chamber 56 in the direction of the arrow to express fluid medication out of the chamber 56 through nozzle 66 and hypodermic needle 70 held in place on the tip 66 by hub 68.

To fill the fluid chamber 56, the hypodermic needle 70 is typically inserted into a membrane-sealed supply of fluid medication with the plunger 58 fully inserted into chamber 56. By withdrawing the plunger 58 by pulling ring 34 connected to the distal or rear end of plunger 58 by a pressure indicator assembly 31 which is described in detail hereinabove with respect to FIG. 2, fluid medication is drawn into chamber 56. To inject the fluid, the hypodermic needle 70 is appropriately placed into the body tissue and then forward pressure is applied in the direction of the arrow to the thumb ring 34 to force the plunger 58 further into the fluid chamber 56 expressing fluid medication from the hypodermic needle 70.

As previously described, further pressure applied to the thumb ring 34 will cause the piston 60 to be further advanced into the chamber 56 so that the fluid medication within the fluid chamber 56 becomes pressurized as the liquid medication is ejected from the needle 70. Upon release of the thumb ring 34, fluid pressure within the fluid chamber 56 is reduced to zero. Further details of the functioning of the pressure indicator assembly 31 with respect to this embodiment 50 are as previously described hereinabove.

While the instant invention has been shown and described herein in what are conceived to be the most practical and preferred embodiments, it is recognized that departures may be made therefrom within the scope of the invention, which is therefore not to be limited to the details disclosed herein, but is to be afforded the full scope of the claims so as to embrace any and all equivalent apparatus and articles.

What is claimed is:

1. A syringe for use with a plunger-type cartridge ampule of the type including a tubular body filled with injectable fluid having a first end closed by a moveable piston member and a second end closed by a flexible resilient membrane, said syringe comprising:

an elongated body member having a cavity for accommodating one cartridge ampule therewithin and having axially disposed front and rear openings thereof;

an elongated plunger having front and rear ends and extending into said cavity through said rear opening and thusly held for slidable translation longitudinally with respect to said body member;

said plunger including a head at said front end thereof positioned within said cavity for engagement against and slidable movement of the piston member longitudinally within the tubular body and a manually engageable thumb actuator including an aperture, connected at said rear end for longitudinal movement of said plunger forcing said head of said plunger into the tubular body;

means for connecting a hypodermic needle in axial alignment to said body member adjacent said front opening, such that when connected one end of the needle would be capable of extending through the flexible membrane into fluid communication with the injectable fluid; and said plunger further including a pressure indicator member mounted for limited longitudinal translation within said rear end and a spring bias means for maintaining said pressure indicator member in an at-rest position when no manual pressure is being applied against said thumb actuator;

said pressure indicator member extending rearwardly through said aperture in said thumb actuator and for placement against the thumb of an operator in proportion to an amount of thumb pressure being applied against said thumb actuator by the operator to express the injectable fluid from the ampule by movement of the moveable piston member whereby the operator is provided with thumb-sensed indicia of fluid injection pressure level in the ampule.

2. In a syringe for use with a plunger-type cartridge ampule of the type including a tubular body filled with injectable fluid having a first end closed by a moveable piston member and a second end closed by a flexible resilient membrane, said syringe comprising an elongated body member having a cavity for accommodating one cartridge ampule therewithin and having axially disposed front an rear openings thereof, and elongated plunger having front and rear ends and extending into said cavity through said rear opening and thusly held for slidable translation longitudinally with respect to said body member, said plunger including a head at said front end thereof positioned within said cavity for engagement against and slidable movement of the piston member longitudinally within the tubular body and a manually engageable thumb actuator including an aperture, connected at said rear end for longitudinal movement of said plunger forcing said head of said body member adjacent said front opening, one end of the needle extending through the flexible membrane into fluid communication with the injectable fluid, the improvement comprising:

an elongated pressure indicator member defining said rearward end of said plunger and positioned within a housing immediately adjacent said thumb actuator for limited longitudinal translation with respect to said thumb actuator;

a spring bias means within said housing for maintaining said pressure indicator member in an at-rest concealed position when no manual pressure is being applied against said thumb actuator;

said pressure indicator member moving to become extended rearwardly within said housing through said aperture in said thumb actuator and for placement against the thumb of an operator in proportion to an amount of thumb pressure being applied against said thumb actuator by the operator to express the injectable fluid, by movement of the moveable piston member whereby the operator is provided with thumb-sensed indicia of fluid injection pressure level.

3. A syringe of the type including a tubular body filled with injectable fluid having a first end closed by a moveable piston and a second end closed by a hypodermic needle, said syringe comprising:

an elongated body member having a fluid chamber having axially disposed front and rear openings thereof;

an elongated plunger having front and rear ends and extending into said fluid chamber through said rear opening and thusly held for slidable translation longitudinally with respect to said body member;

said plunger including a piston at said front end thereof positioned within said fluid chamber for sealed slidable movement of the piston longitudinally within the tubular body and a manually engageable thumb actuator including an aperture, connected at said rear end for longitudinal movement of said plunger forcing said piston into said fluid chamber;

means for connecting a hypodermic needle in axial alignment to said body member adjacent said front opening, such that when connected one end of the needle would be capable of extending into fluid communication with the injectable fluid; and said plunger further including a pressure indicator member mounted for limited longitudinal translation within said rear end and a spring bias means for maintaining said pressure indicator member in an at-rest position when no manual pressure is being applied against said thumb actuator;

said pressure indicator member extending rearwardly through said aperture in said thumb actuator and for placement against the thumb of an operator in proportion to an amount of thumb pressure being applied against said thumb actuator by the operator to express the injectable fluid from said fluid chamber by movement of the moveable piston whereby the operator is provided with thumb-sensed indicia of fluid injection pressure level in said fluid chamber.

4. In a syringe of the type including a tubular body member fillable with injectable fluid having a first end closed by a moveable piston and a second end closed by a hypodermic needle, said syringe comprising an elongated body member having a fluid chamber and axially disposed front and rear openings thereof, and elongated plunger having front and rear ends and extending into said fluid chamber through said rear opening and thusly held for slidable translation longitudinally with respect to said body member, said plunger including said piston at said front end thereof positioned within said fluid chamber for engagement against and slidable movement of said piston member longitudinally within said fluid chamber and a manually engageable thumb actuator including an aperture, connected at said rear end for longitudinal movement of said plunger forcing said piston into the tubular body, means for connecting the hypodermic needle in axial alignment to said body member adjacent said front opening, the improvement comprising:

an elongated pressure indicator member defining said rearward end of said plunger and positioned within a housing immediately adjacent said thumb actuator for limited longitudinal translation with respect to said thumb actuator;

a spring bias means within said housing for maintaining said pressure indicator member in an at-rest concealed position when no manual pressure is being applied against said thumb actuator;

said pressure indicator member moving to become extended rearwardly with said housing through said aperture in said thumb actuator and against the thumb of an operator in proportion to an amount of thumb pressure being applied against said thumb actuator by the operator to express the injectable fluid from said fluid chamber by movement of the moveable piston member whereby the operator is provided with thumb-sensed indicia of fluid injection pressure level within said fluid chamber.

* * * * *